(12) United States Patent
Fallin

(10) Patent No.: US 11,596,461 B2
(45) Date of Patent: *Mar. 7, 2023

(54) SYSTEM AND METHOD FOR ORTHOPEDIC IMPLANT CONFIGURATION

(71) Applicant: Stryker European Operations Holdings LLC, Kalamazoo, MI (US)

(72) Inventor: T. Wade Fallin, Hyde Park, UT (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 115 days.

This patent is subject to a terminal disclaimer.

(21) Appl. No.: 17/147,720

(22) Filed: Jan. 13, 2021

(65) Prior Publication Data
US 2021/0128215 A1 May 6, 2021

Related U.S. Application Data

(60) Continuation of application No. 15/932,285, filed on Feb. 16, 2018, now Pat. No. 10,898,251, which is a
(Continued)

(51) Int. Cl.
*A61B 17/70* (2006.01)
*A61B 17/88* (2006.01)

(52) U.S. Cl.
CPC ...... *A61B 17/8863* (2013.01); *A61B 17/7074* (2013.01)

(58) Field of Classification Search
CPC ...................................... A61B 17/7074–7092
See application file for complete search history.

(56) References Cited

U.S. PATENT DOCUMENTS

| 4,409,968 A | 10/1983 | Drummond |
| 4,474,046 A | 10/1984 | Cook |

(Continued)

FOREIGN PATENT DOCUMENTS

| DE | 4238339 A1 | 5/1994 |
| DE | 29710979 U1 | 8/1997 |

(Continued)

OTHER PUBLICATIONS

Charles Hartjen; The Atavi System, Surgical Technique Brochure. Endius, p. 1-17, undated.

(Continued)

*Primary Examiner* — Eduardo C Robert
*Assistant Examiner* — Steven J Cotroneo
(74) *Attorney, Agent, or Firm* — Lerner, David, Littenberg, Krumholz & Mentlik, LLP

(57) ABSTRACT

Anatomic points within the body are projected outside the body through the use of extenders. The projected points may then be used for measurement, or to facilitate the selection or configuration of an implant that is to be positioned proximate the anatomic points. Such an implant may be a rod for a posterior spinal fusion system. Pedicle screws may be implanted into pedicles of the spine, and may then serve as anchors for the extenders. The extenders may have rod interfaces that receive the rod in a manner that mimics the geometry of the pedicle screws so that the selected or configured contoured rod will properly fit into engagement with the pedicle screws.

19 Claims, 13 Drawing Sheets

Related U.S. Application Data continuation of application No. 13/444,231, filed on Apr. 11, 2012, now Pat. No. 9,895,182, which is a division of application No. 11/178,035, filed on Jul. 8, 2005, now Pat. No. 8,177,817.

(60) Provisional application No. 60/682,344, filed on May 18, 2005.

(56) References Cited

U.S. PATENT DOCUMENTS

| | | | |
|---|---|---|---|
| 4,653,481 A | 3/1987 | Howland et al. | |
| 4,887,595 A | 12/1989 | Heinig et al. | |
| 4,957,495 A | 9/1990 | Kluger | |
| 5,171,279 A | 12/1992 | Mathews | |
| 5,242,443 A | 9/1993 | Kambin | |
| D346,217 S | 4/1994 | Sparker et al. | |
| 5,357,983 A | 10/1994 | Mathews | |
| 5,360,431 A | 11/1994 | Puno et al. | |
| 5,373,860 A | 12/1994 | Catone | |
| 5,409,488 A | 4/1995 | Ulrich | |
| 5,425,732 A | 6/1995 | Ulrich | |
| 5,490,409 A | 2/1996 | Weber | |
| 5,496,322 A | 3/1996 | Mathews | |
| 5,569,248 A | 10/1996 | Mathews | |
| 5,591,165 A | 1/1997 | Jackson | |
| 5,624,442 A | 4/1997 | Mellinger et al. | |
| 5,658,286 A | 8/1997 | Sava | |
| 5,720,751 A | 2/1998 | Jackson | |
| 5,728,097 A | 3/1998 | Mathews | |
| 5,814,046 A | 9/1998 | Hopf et al. | |
| RE36,221 E | 6/1999 | Breard et al. | |
| 5,938,662 A | 8/1999 | Rinner | |
| 5,964,761 A * | 10/1999 | Kambin | A61B 17/7007 606/280 |
| 5,976,146 A | 11/1999 | Ogawa et al. | |
| 6,015,409 A | 1/2000 | Jackson | |
| 6,033,406 A | 3/2000 | Mathews | |
| 6,035,691 A | 3/2000 | Lin et al. | |
| 6,090,113 A * | 7/2000 | Le Couedic | A61B 17/708 606/86 A |
| 6,123,707 A | 9/2000 | Wagner | |
| 6,159,179 A | 12/2000 | Simonson | |
| 6,175,758 B1 | 1/2001 | Kambin | |
| 6,183,472 B1 | 2/2001 | Lutz | |
| 6,200,322 B1 | 3/2001 | Branch et al. | |
| 6,235,028 B1 * | 5/2001 | Brumfield | A61B 17/88 606/53 |
| 6,332,780 B1 | 12/2001 | Traxel et al. | |
| 6,485,518 B1 | 11/2002 | Cornwall et al. | |
| 6,506,151 B2 | 1/2003 | Estes et al. | |
| 6,530,929 B1 | 3/2003 | Justis et al. | |
| 6,596,008 B1 | 7/2003 | Kambin | |
| 6,607,530 B1 | 8/2003 | Carl et al. | |
| 6,723,095 B2 | 4/2004 | Hammerslag | |
| 6,740,089 B2 | 5/2004 | Haider | |
| 6,749,614 B2 | 6/2004 | Teitelbaum et al. | |
| 6,821,277 B2 | 11/2004 | Teitelbaum | |
| 6,875,212 B2 | 4/2005 | Shaolian et al. | |
| 6,899,713 B2 | 5/2005 | Shaolian et al. | |
| 6,923,811 B1 | 8/2005 | Carl et al. | |
| 6,929,647 B2 | 8/2005 | Cohen | |
| 6,964,667 B2 | 11/2005 | Shaolian et al. | |
| 7,008,422 B2 | 3/2006 | Foley et al. | |
| 7,008,424 B2 | 3/2006 | Teitelbaum | |
| 7,011,660 B2 | 3/2006 | Sherman et al. | |
| 7,083,621 B2 | 8/2006 | Shaolian et al. | |
| 7,160,300 B2 | 1/2007 | Jackson | |
| 7,188,626 B2 | 3/2007 | Foley et al. | |
| 7,250,052 B2 | 7/2007 | Landry et al. | |
| 7,476,240 B2 | 1/2009 | Raymond et al. | |
| 7,666,189 B2 * | 2/2010 | Gerber | A61B 17/7083 606/86 A |
| 7,758,617 B2 * | 7/2010 | Iott | A61B 17/7086 606/255 |
| 7,811,288 B2 | 10/2010 | Jones et al. | |
| 7,955,355 B2 | 6/2011 | Chin | |
| 3,002,798 A1 | 8/2011 | Chin et al. | |
| 8,105,361 B2 | 1/2012 | Anderson et al. | |
| 8,177,817 B2 | 5/2012 | Fallin | |
| 8,192,440 B2 | 6/2012 | Jones et al. | |
| 8,894,655 B2 | 11/2014 | Fallin et al. | |
| 10,898,251 B2 * | 1/2021 | Fallin | A61B 17/8863 |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0161367 A1 | 10/2002 | Ferree | |
| 2002/0161368 A1 | 10/2002 | Foley et al. | |
| 2002/0198526 A1 | 12/2002 | Shaolian et al. | |
| 2003/0045874 A1 * | 3/2003 | Thomas, Jr. | A61B 17/7049 606/264 |
| 2003/0060824 A1 | 3/2003 | Viart et al. | |
| 2003/0060826 A1 | 3/2003 | Foley et al. | |
| 2003/0199884 A1 | 10/2003 | Davison et al. | |
| 2003/0225408 A1 | 12/2003 | Nichols et al. | |
| 2004/0006341 A1 | 1/2004 | Shaolian et al. | |
| 2004/0006344 A1 | 1/2004 | Nguyen et al. | |
| 2004/0034351 A1 | 2/2004 | Sherman et al. | |
| 2004/0039384 A1 | 2/2004 | Boehm et al. | |
| 2004/0059333 A1 | 3/2004 | Carl et al. | |
| 2004/0082954 A1 | 4/2004 | Teitelbaum et al. | |
| 2004/0082961 A1 | 4/2004 | Teitelbaum | |
| 2004/0087950 A1 | 5/2004 | Teitelbaum | |
| 2004/0092934 A1 | 5/2004 | Howland | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0172022 A1 | 9/2004 | Landry et al. | |
| 2004/0215190 A1 | 10/2004 | Nguyen et al. | |
| 2004/0215193 A1 | 10/2004 | Shaolian et al. | |
| 2004/0260287 A1 | 12/2004 | Ferree | |
| 2004/0267279 A1 | 12/2004 | Casutt et al. | |
| 2005/0010220 A1 | 1/2005 | Casutt et al. | |
| 2005/0021031 A1 | 1/2005 | Foley et al. | |
| 2005/0021040 A1 * | 1/2005 | Bertagnoli | A61B 17/708 606/90 |
| 2005/0038432 A1 | 2/2005 | Shaolian et al. | |
| 2005/0043742 A1 | 2/2005 | Bruneau et al. | |
| 2005/0065517 A1 * | 3/2005 | Chin | A61B 17/7089 606/279 |
| 2005/0070917 A1 | 3/2005 | Justis | |
| 2005/0124991 A1 | 6/2005 | Jahng | |
| 2005/0131407 A1 | 6/2005 | Sicvol et al. | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0149022 A1 | 7/2005 | Shaolian et al. | |
| 2005/0154389 A1 | 7/2005 | Selover et al. | |
| 2005/0165396 A1 | 7/2005 | Fortin et al. | |
| 2005/0171540 A1 | 8/2005 | Lim et al. | |
| 2005/0245928 A1 | 11/2005 | Colleran et al. | |
| 2005/0251139 A1 | 11/2005 | Roh | |
| 2005/0277934 A1 | 12/2005 | Vardiman | |
| 2006/0030839 A1 | 2/2006 | Park et al. | |
| 2006/0030858 A1 | 2/2006 | Simonson et al. | |
| 2006/0030861 A1 | 2/2006 | Simonson et al. | |
| 2006/0095035 A1 | 5/2006 | Jones et al. | |
| 2006/0111713 A1 | 5/2006 | Jackson | |
| 2006/0111714 A1 | 5/2006 | Foley | |
| 2006/0200135 A1 | 9/2006 | Sherman et al. | |
| 2006/0217735 A1 | 9/2006 | MacDonald et al. | |
| 2006/0247658 A1 | 11/2006 | Pond et al. | |
| 2006/0264934 A1 | 11/2006 | Fallin | |
| 2006/0264962 A1 | 11/2006 | Chin et al. | |
| 2006/0293680 A1 | 12/2006 | Jackson | |
| 2007/0043359 A1 | 2/2007 | Altarac et al. | |
| 2007/0083210 A1 | 4/2007 | Hestad et al. | |
| 2007/0118119 A1 | 5/2007 | Hestad | |
| 2008/0009864 A1 | 1/2008 | Forton et al. | |
| 2009/0099605 A1 | 4/2009 | Fallin et al. | |
| 2009/0216328 A1 | 8/2009 | Birkmeyer et al. | |
| 2009/0228056 A1 | 9/2009 | Jackson | |
| 2010/0137915 A1 | 6/2010 | Anderson et al. | |
| 2010/0331901 A1 | 12/2010 | Iott et al. | |

(56) References Cited

U.S. PATENT DOCUMENTS

| | | | |
|---|---|---|---|
| 2011/0015678 | A1 | 1/2011 | Jackson |
| 2011/0077692 | A1 | 3/2011 | Jackson |
| 2011/0152940 | A1* | 6/2011 | Frigg ............... A61B 17/7002 606/264 |
| 2011/0238120 | A1 | 9/2011 | Chin |
| 2011/0245884 | A9 | 10/2011 | Brumfield et al. |
| 2012/0089191 | A1 | 4/2012 | Altarac et al. |
| 2012/0123477 | A1 | 5/2012 | Landry et al. |
| 2012/0158070 | A1 | 6/2012 | Jackson |

FOREIGN PATENT DOCUMENTS

| | | | |
|---|---|---|---|
| DE | 19726754 A1 | 2/1999 | |
| DE | 10027988 | 1/2002 | |
| EP | 0528177 | 2/1993 | |
| EP | 1468652 | 10/2004 | |
| JP | 10248855 A * | 9/1998 | ........... A61B 17/708 |
| JP | 2005169064 A * | 6/2005 | ......... A61B 17/7034 |
| SU | 839513 A1 | 6/1981 | |
| WO | 9514437 | 6/1995 | |
| WO | 0141681 A1 | 6/2001 | |
| WO | 03020110 | 3/2003 | |
| WO | 04004584 | 1/2004 | |
| WO | 04017847 | 3/2004 | |
| WO | 04041100 A1 | 5/2004 | |
| WO | 2004058045 | 7/2004 | |
| WO | 2005020832 A1 | 3/2005 | |
| WO | 05032358 | 4/2005 | |
| WO | 05060534 A2 | 7/2005 | |

OTHER PUBLICATIONS

Communication from corresponding European Application, 06 76 0048, dated Sep. 29, 2009.
Examination report from corresponding European Application, 06 76 0048, dated Aug. 20, 2008.
Kambin et al., Anterior Column Support for Failed Fusion, Revision Spine Surgery, pp. 589-600, published Jan. 1999.
Kambin, Minimally Invasive Techniques in Spinal Surgery Current Practice, Neurosurgical Focus, wwwspineuniversecom, 16 pages, printed Aug. 24, 2005.
Kambin, The Role of Minimally Invasive Surgery in Spinal Disorders, Advance Operative Orthopedics, vol. 3, pp. 147-171, Dec. 1994.
Office Action from U.S. Appl. No. 11/526,785, dated Jan. 8, 2009.
Office Action from U.S. Appl. No. 11/526,785, dated Sep. 3, 2009.
Pathfinder; Minimally Invasive Pedicie Fixation System. Spinal Concepts Product Brochure p. 1-4, May 2003.
Pathfinder; Minimally invasive Spinal Fixation System and Surgical Technique. Spinal Concepts Product Brochure, p. 1-26, undated.
Sofamor Danek; Sextant CD Horizon Sextant Rod Insertion System, Surgical Technique, Techniques, p. 1-29, 2003.
U.S. Appl. No. 11/526,785, filed Sep. 25, 2006.
U.S. Appl. No. 12/316,637, filed Dec. 15, 2008.
U.S. Appl. No. 11/904,029, filed Sep. 25, 2007.
U.S. Appl. No. 11/904,030, filed Sep. 25, 2007.

* cited by examiner

SYSTEM AND METHOD FOR ORTHOPEDIC IMPLANT CONFIGURATION

CROSS-REFERENCE TO RELATED APPLICATIONS

The present application is a continuation of U.S. patent application Ser. No. 15/932,285, filed Feb. 16, 2018, which is a continuation of U.S. patent application Ser. No. 13/444,231, filed Apr. 11, 2012, which is a divisional of U.S. patent application Ser. No. 11/178,035, filed Jul. 8, 2005, which claims the benefit of the filing date of U.S. Provisional Patent Application No. 60/682,344, filed May 18, 2005, the disclosures of which are hereby incorporated herein by reference.

BACKGROUND OF THE INVENTION

The present invention relates generally to the selection and/or configuration of implantable devices, and more precisely, to posterior spinal fusion systems.

A wide variety of orthopedic implants exist. Such implants are typically anchored to bones within the body. Every person has different bone structure; accordingly, implants must vary considerably in geometry to meet the needs of a broad range of patients. Although visualization methods such as X-Rays and fluoroscopy can be utilized to help determine bone geometry, contact with the bones must often be made in order to provide a sufficiently accurate measurement of bony landmarks. Current procedures often involve the exposure of a relatively large area to permit such measurement.

According to new minimally invasive surgical (MIS) procedures, many orthopedic implants can be secured to bone through relatively small incisions. Unfortunately, if a larger incision must be made to permit bone measurement and implant selection or configuration, most of the beneficial effects of the MIS implantation procedure will be lost. Accordingly, there is a need in the art for bony landmark measurement and implant selection or configuration methods that can be carried out through small incisions. Such methods should be relatively simple and quick to perform, with comparatively simple instrumentation.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for configuring and/or selecting devices to be implanted in the body. Although the examples provided herein generally relate to contouring a rod for a posterior spinal fusion system, the present invention may be applied to any procedure in which the relative position and/or orientations of internal anatomic locations are to be measured or used to configure or select an implant. Accordingly, the scope of the present invention is not intended to be limited by the examples discussed herein, but only by the appended claims.

In this application, an "anatomic point" is a location within the body. An anatomic point need not be located on any specific anatomic structure. When applied to anatomy, "proximal" refers to a position relatively closer to the center of the body, and "distal" refers to a position relatively further from the center of the body. However, when referred to a tool or similar implement, "proximal" refers to a portion relatively nearer the operator of the tool or similar implement, and "distal" refers to a portion relatively further from the operator.

The phrase "spatial transformation" refers to any mathematical procedure in which one or more coordinates can be transformed in a manner that permits the original coordinates to be determined based on the results of the transformation. Accordingly, a spatial transformation may involve any combination of translation and rotation of the original coordinates, as long as the transformation can be analytically reversed to permit the original coordinates to be obtained. A "translational spatial transformation" is a spatial transformation in which the original coordinates are all uniformly translated along the same vector.

The term "mate" refers to any type of connection in which cooperating features engage each other to restrict relative motion of the mating parts. The term "couple" is not limited to fixed attachment, but also includes sliding attachment and the like. The term "receive" does not require one item to completely capture another; rather, one item receives another if the first item engages the second item in a manner that restricts relative motion of the items.

Figure 1:
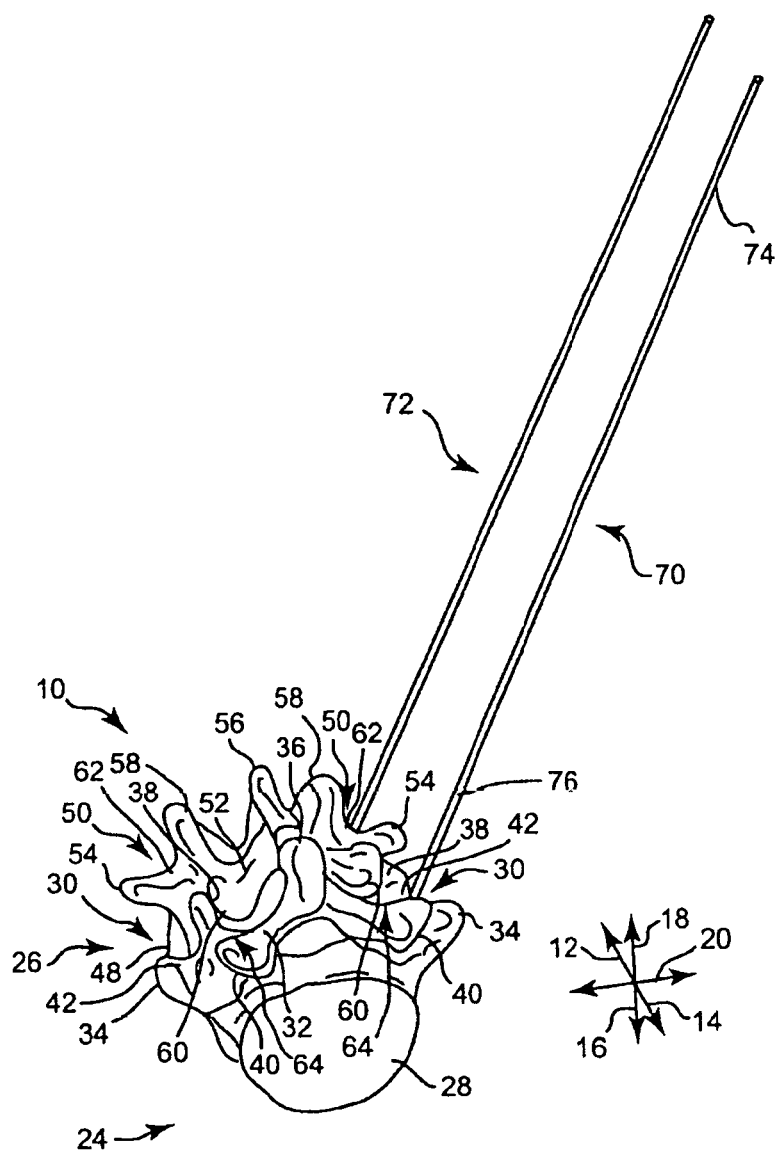
FIG. 1 is a perspective view of two adjacent vertebrae of a spine, with guide wires implanted in the pedicles of the right side.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. Additionally, the first vertebra 24 has inferior facets 40, which are positioned toward the bottom of the first vertebra 24 and face generally laterally. Each of the pedicles 30 of the first vertebra 24 has a saddle point 42, which is positioned generally at the center of the juncture of each superior facet 38 with the adjacent transverse process 34.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54, each of which extends from the corresponding pedicle 50 generally along the medial/lateral axis 20, and a spinous process 56 that extends from the lamina 52 along the posterior direction 18.

The second vertebra 26 also has a pair of superior facets 58, which are positioned toward the top of the second vertebra 26 and face generally inward. Additionally, the second vertebra 26 has inferior facets 60, which are positioned toward the bottom of the second vertebra 26 and face generally outward. Each of the pedicles 60 of the second vertebra 26 has a saddle point 62, which is positioned generally at the center of the juncture of each superior facet 58 with the adjacent transverse process 54.

The superior facets 38 of the first vertebra 24 articulate (i.e., slide and/or press) with the inferior facets 60 of the second vertebra 26 to limit relative motion between the first and second vertebrae 24, 26. Thus, the combination of each superior facet 38 with the adjacent inferior facet 60 provides a facet joint 64. The first and second vertebrae 24, 26 thus define two facet joints 64 that span the distance between the first and second vertebrae 24, 26. The inferior facets 40 of the first vertebra 40 and the superior facets 58 of the second vertebra 26 are part of other facet joints that control motion between the first and second vertebrae 24, 26 and adjacent vertebrae (not shown) and/or the sacrum (also not shown).

Figure 11:
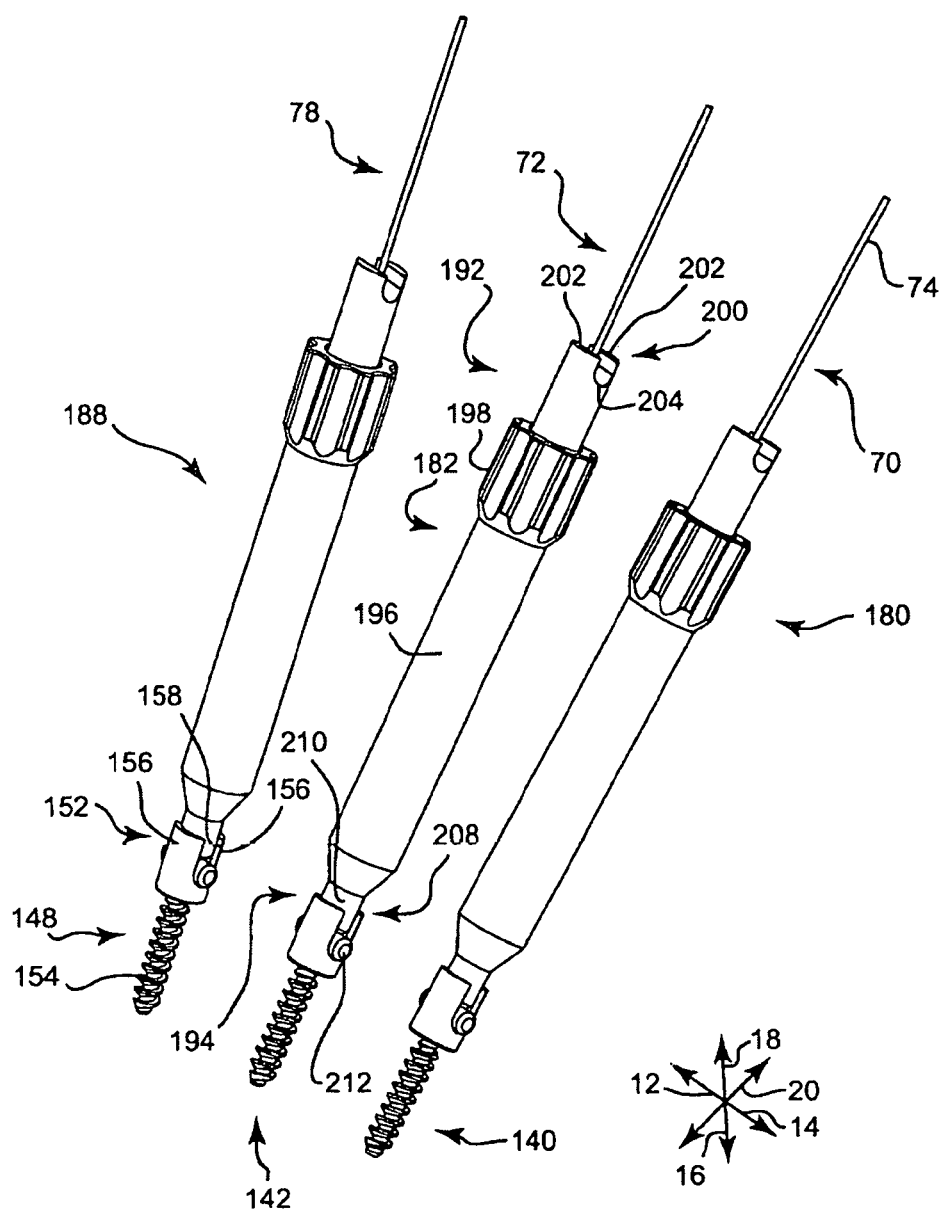
FIG. 11 is a perspective view of the guide wires of FIG. 2, with pedicle screws installed and extenders engaging the pedicle screws and guide wires without the use of cannulas, according to one alternative method of the invention.
Figure 12:
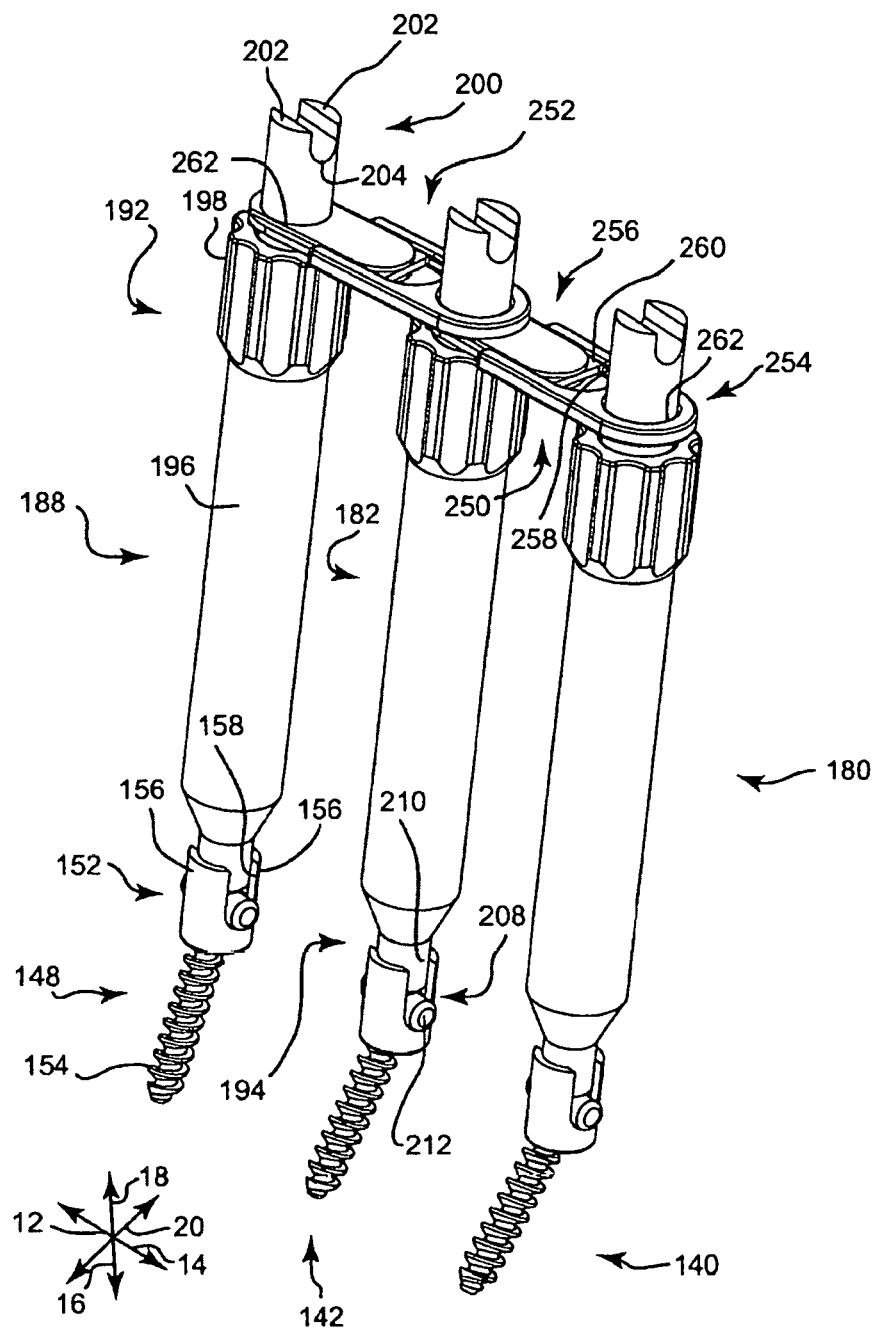
FIG. 12 is a perspective view of the pedicle screws and extenders of FIG. 11, with bridges used to keep the extenders in a parallel configuration.
Figure 13:
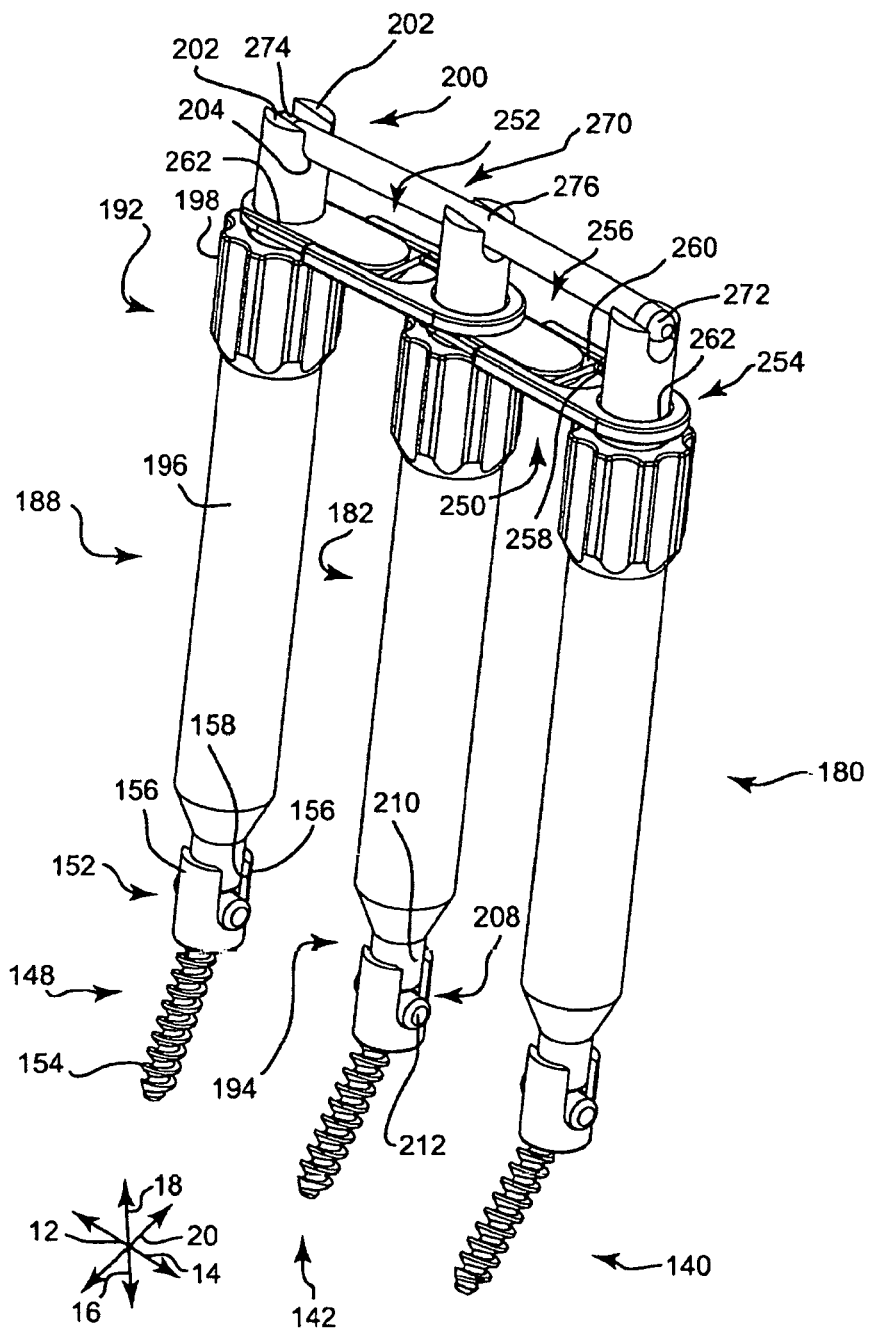
FIG. 13 is a perspective view of the pedicle screws, extenders, and bridges of FIG. 12, with a rod seated in the rod interfaces of the extenders for contouring.

The vertebrae 24, 26 and/or the intervertebral disc (not shown) between them, may be damaged or diseased in some manner that makes it desirable to secure the vertebrae 24, 26 together in a manner that prevents relative motion between them. Accordingly, posterior spinal fusion may be employed to secure the pedicles 30, 50 together. FIGS. 1 through 10 illustrate one method of configuring and installing a posterior spinal fusion system. FIGS. 11 through 13 illustrate steps that may be employed in place of the steps of FIGS. 6 through 9.

As further illustrated in FIG. 1, a first guide wire 70 has been inserted into the right-side pedicle 30 of the first vertebra 24, and a second guide wire 72 has been inserted into the right-side pedicle 50 of the second vertebra 26. The guide wires 70, 72 pass through the saddle points 42, 62, respectively, of the pedicles 30, 50. Each of the guide wires 70, 72 has a proximal end 74 and a distal end 76. As shown, the proximal ends 74 are exposed, and the distal ends 76 are implanted in the pedicles 30, 50. The distal ends 76 may be implanted by methods known in the surgical arts.

Figure 2:
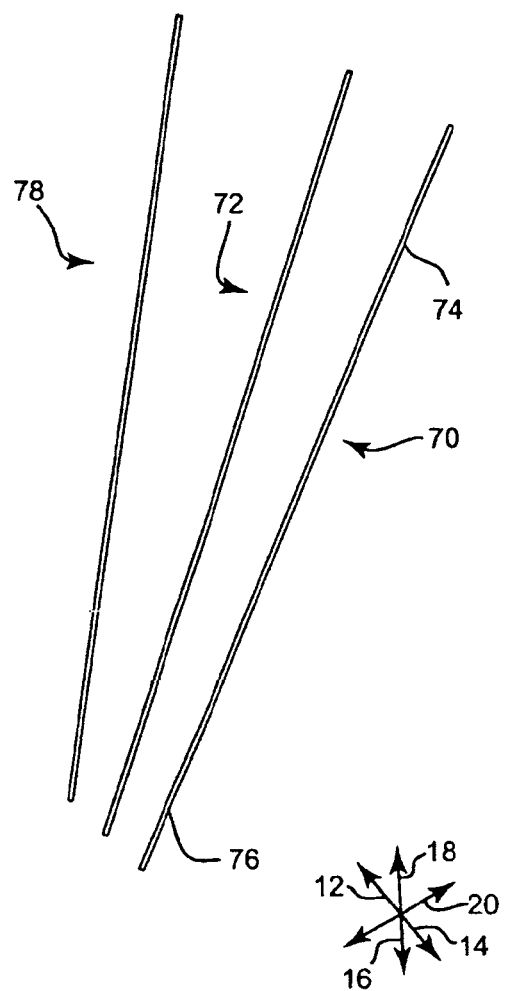
FIG. 2 is a perspective view of three guide wires in isolation, positioned as though implanted in the pedicles of the right sides of three adjacent vertebrae.

Referring to FIG. 2, a perspective view illustrates the first and second guide wires 70, 72 of FIG. 1, with the vertebrae 24, 26 removed for clarity. A third guide wire 78 is also shown. The third guide wire 78 is positioned adjacent to the first and second guide wires 70, 72 as though the third guide wire 78 were implanted in the right-hand pedicle of a vertebra (not shown) directly superior to the second vertebra 26. Accordingly, the method of FIGS. 1 through 10 may be used to secure together vertebrae on multiple levels, not just two adjacent vertebrae.

Figure 3:
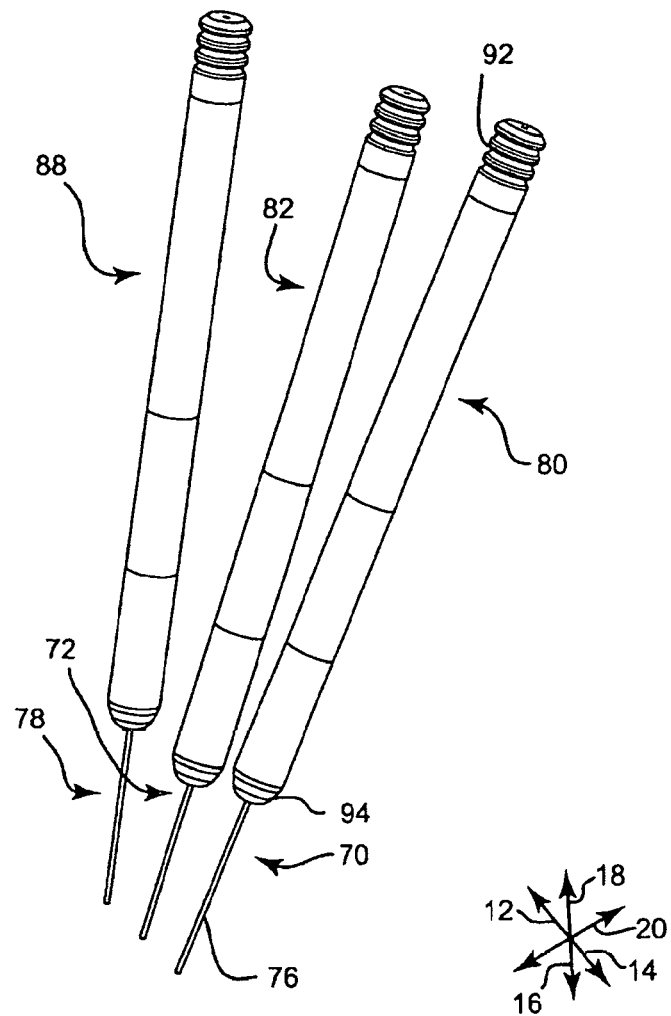
FIG. 3 is a perspective view of the guide wires of FIG. 2, with dilators advanced along the guide wires to dilate surrounding tissue.

Referring to FIG. 3, a perspective view illustrates the guide wires 70, 72, 78, in conjunction with a first dilator 80, a second dilator 82, and a third dilator 88. Each of the dilators 80, 82, 88 has a proximal end 92 and a distal end 94. The proximal ends 92 may be shaped for gripping by hand, or for attachment to a handle or the like. The distal ends 94 are rounded to permit relatively gentle spreading of tissues surrounding the guide wires 70, 72, 78 by the dilators 80, 82, 88.

Each of the dilators 80, 82, 88 has a bore sized to receive the proximal end 74 of the corresponding guide wire 70, 72, or 78, so that the dilators 80, 82, 88 are able to slide along the guide wires 70, 72, 78 toward the distal ends 74, thereby spreading the tissues away from the guide wires 70, 72, 78. As an alternative to the guide wires 70, 72, 78 and the dilators 80, 82, 88, a variety of other guiding devices and/or dilation devices may be used within the scope of the present invention.

Figure 4:
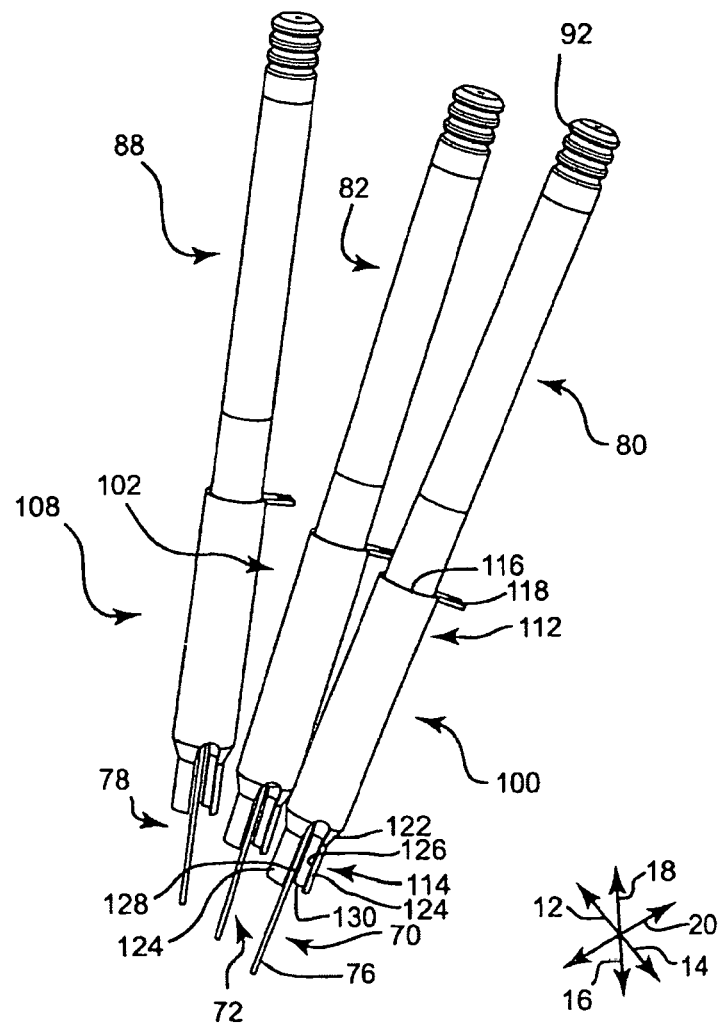
FIG. 4 is a perspective view the guide wires and dilators of FIG. 3, with cannulas positioned around the dilators.

Referring to FIG. 4, a perspective view illustrates the guide wires 70, 72, 78 and dilators 80, 82, 88, with the addition of a first cannula 100, a second cannula 102, and a third cannula 108. Each of the cannulas 100, 102, 108 has a proximal end 112, a distal end 114, with a bore passing between the proximal and distal ends 112, 114. Each proximal end 112 has a port 116 in communication with the bore, and a tab 118 that may facilitate manipulation or securement of the corresponding cannula 100, 102, or 108.

Each distal end 114 has a taper 122 that provides a reduction in the diameter of the cannula 100, 102, or 108 toward the distal end 114. Additionally, each distal end 114 has a pair of arms 124 that extend generally parallel to the axis of the corresponding cannula 100, 102, or 108. The arms 124 define a first slot 126 and a second slot 128 that also extend parallel to the axis of the corresponding cannula 100, 102, 108. The ends of the arms 124 define a port 130 that also communicates with the bore of the cannula 100, 102, or 108.

The cannulas 100, 102, 108 are inserted around the guide wires 70, 72, 78. The cannulas 100, 102, 108 may be placed by withdrawing dilators 80, 82, 88, inserting the cannulas 100, 102, 108 around the proximal ends 74 of the guide wires 70, 72, 78, inserting the distal ends 94 of the dilators 80, 82, 88 into the ports 116 of the proximal end 112 of the cannulas 100, 102, 108, and then advancing the dilators 80, 82, 88 along the guide wires 70, 72, 78 to urge the cannulas 100, 102, 108 toward the distal ends 76 of the guide wires 70, 72, 78, into the dilated tissue.

According to one alternative method, the dilators 80, 82, 88 are removed to permit placement of the cannulas 100, 102, 108, and are not re-inserted. According to other alternative embodiments, cannulas (not shown) may be modular, or may have dilatable distal ends that enable placement of the cannulas around the dilators 80, 82, 88, so that the dilators 80, 82, 88 need not be removed from the guide wires 70, 72, 78 until the cannulas are properly positioned. The present invention is not limited to use of cannulas like those of FIG. 4; rather, any of a variety of cannulas may be used.

Figure 5:
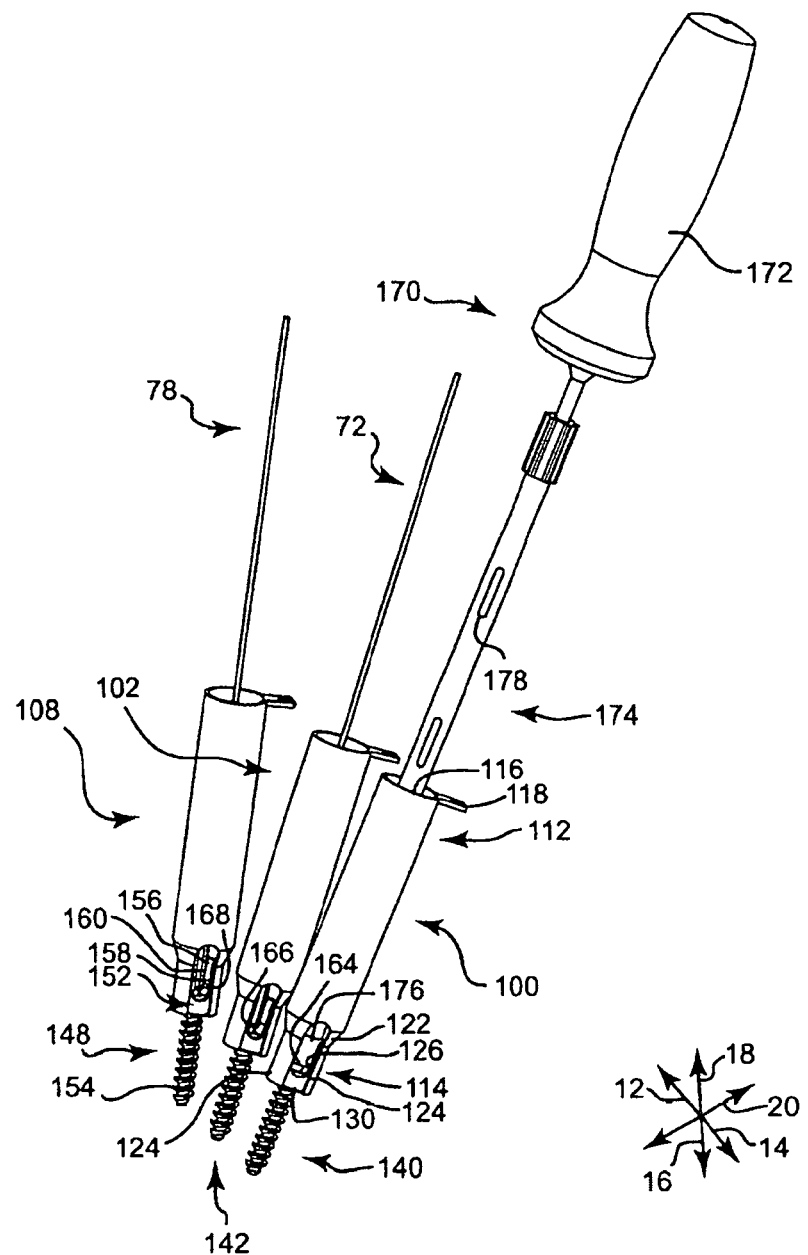
FIG. 5 is a perspective view of the guide wires and cannulas of FIG. 3, with pedicle screws implanted in the pedicles along the guide wires through the use of an insertion tool.

Referring to FIG. 5, a perspective view illustrates the guide wires 70, 72, 78 and cannulas 100, 102, 108, with the addition of connection elements designed to be retained at the distal ends 114 of the cannulas 100, 102, 108. The connection elements may be fixation members designed to anchor a rod to the first vertebra 24, the second vertebra 26, and the third vertebra (not shown in FIG. 5). More precisely, the connection elements may be pedicle screws 140, 142, and 148 implantable in vertebral pedicles.

The pedicle screws 140, 142, 148 may be designed to provide polyaxial coupling to the associated pedicles. Each of the pedicle screws 140, 142, 148 has a cage 152 shaped to receive a rod, and a screw 154 that passes through an aperture (not visible) of the cage 152 in such a manner that the screw 154 is able to extend from the cage 152 along a plurality of relative orientations. Thus, after the screw 154 has been implanted in a pedicle, the orientation of the cage 152 with respect to the screw 154 can still be altered. Each of the screws 154 has a lumen passing along the axis of the screw 154 so that the screws 154 can slide along the guide wires 70, 72, 78 for accurate implantation in the pedicles.

Each cage 152 has two arms 156 that extend generally away from the screw 154 and define a first slot 158 and a second slot 160 through which a rod (not shown in FIG. 5) can pass. The closed ends of the slots 158, 160 are rounded in a manner that corresponds to the radius of the rod to be retained within the cage 152 to facilitate secure retention of the rod. The inward-facing surfaces of the arms 156 may be threaded to enable the arms 156 may be threaded to enable the arms 156 to receive a nut (not shown in FIG. 5). Tightening of the nut then presses the rod against the head (not shown) of the screw 154 to keep the rod in place within the slots 158, 160, and to lock the orientation of the screw 154 with respect to the cage 152.

The pedicle screws 140, 142, 148 represent only one of many types of connection elements that may be used in connection with the present invention. A variety of known devices may be used to secure a rod to a plurality of vertebra to provide posterior fusion.

Upon implantation in the pedicles, the pedicle screws 140, 142, 148 are positioned such that a first anatomic point 164, a second anatomic point 166, and a third anatomic point 168 are within the cages 152 of the first pedicle screw 140, the second pedicle screw 142, and the third pedicle screw 148, respectively. Upon installation of the rod, the axis of the rod is to pass through the anatomic points 164, 166, 168.

The pedicle screws 140, 142, 148 may be installed in a variety of ways. According to one method, the dilators 80, 82, 88 are first removed. Then, each of the pedicle screws 140, 142, 148 is implanted through the use of an insertion tool 170. The insertion tool 170 has a handle 172 designed to be gripped by hand, and a stem 174 extending from the handle 172. The stem 174 has a distal end 176 shaped to engage the head of each of the screws 154. According to one example, the head of each of the screws 154 has a hexagonal recess (not visible), and the distal end 176 has a corresponding hexagonal male feature (not visible). Thus, torque applied to the handle 172 can be transmitted to each of the screws 154.

The stem 174 also has a lumen (not shown) sized to fit around each of the guide wires 70, 72, 78 so that the guide wires 70, 72, 78 can be used to guide implantation of the screws 154 through the use of the insertion tool 170. Slots 178 provide access to the lumen for cleaning.

Each of the screws 154 is coupled to the insertion tool 170 by connecting the head of the screw 154 to the distal end 176 of the stem 174. The insertion tool 170 is then moved to insert the proximal end 74 of the corresponding guide wire 70, 72, 78 through the lumen of the screw 154 and into the lumen of the stem 174. The insertion tool 170 is used to insert the pedicle screw 140, 142, or 148 through the corresponding cannula 100, 102, or 108 until the screw 154 contacts the first pedicle 30, the second pedicle 50, or the third pedicle. Then, torque and axial pressure are applied to the handle 172 to embed the threads of the screw 154 into the bone. The same method may be used to implant all three of the pedicle screws 140, 142, 148. After the pedicle screws 140, 142, 148 have been implanted, the guide wires 70, 72, 78 may be removed.

The cages 152 may be sized to fit relatively snugly within the ports 130 at the distal ends 114 of the cannulas 100, 102, 108. The arms 124 of each distal end 114 thus form a docking feature that enables the corresponding pedicle screw 140, 142, or 148 to dock with the distal end 114 of the corresponding cannula 100, 102, 108. The cages 152 are then constrained to be coaxial with the cannulas 100, 102, 108.

Figure 6:
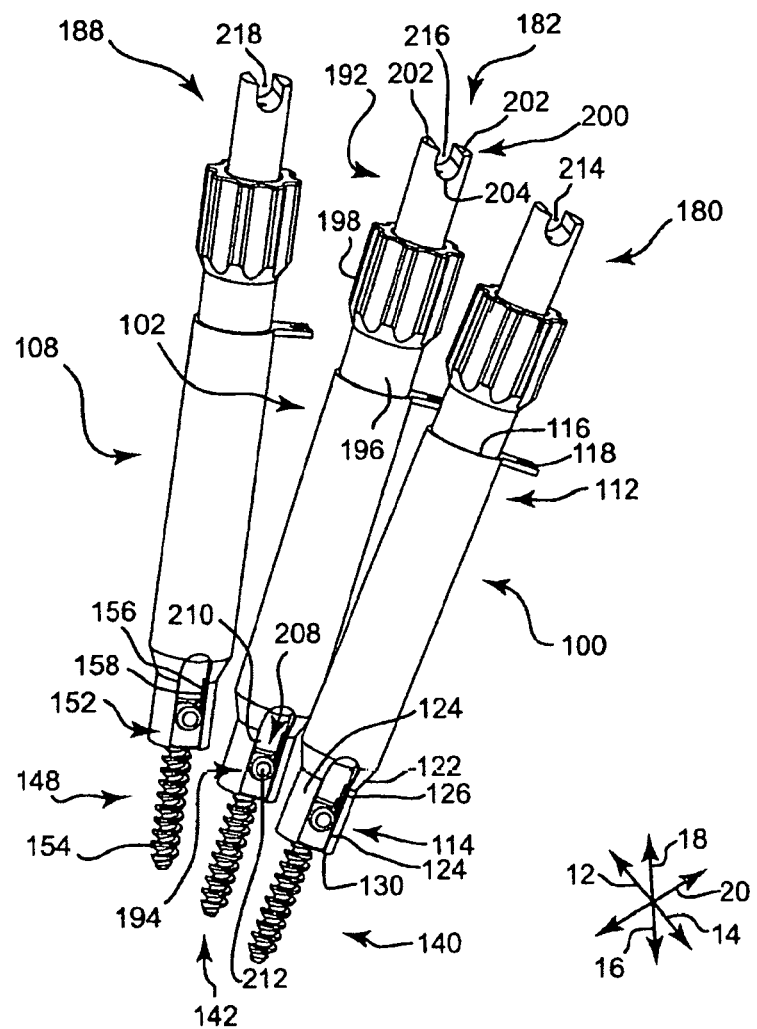
FIG. 6 is a perspective view of the cannulas and pedicle screws of FIG. 5, with extenders positioned in engagement with the cannulas and pedicle screws.
Figure 7:
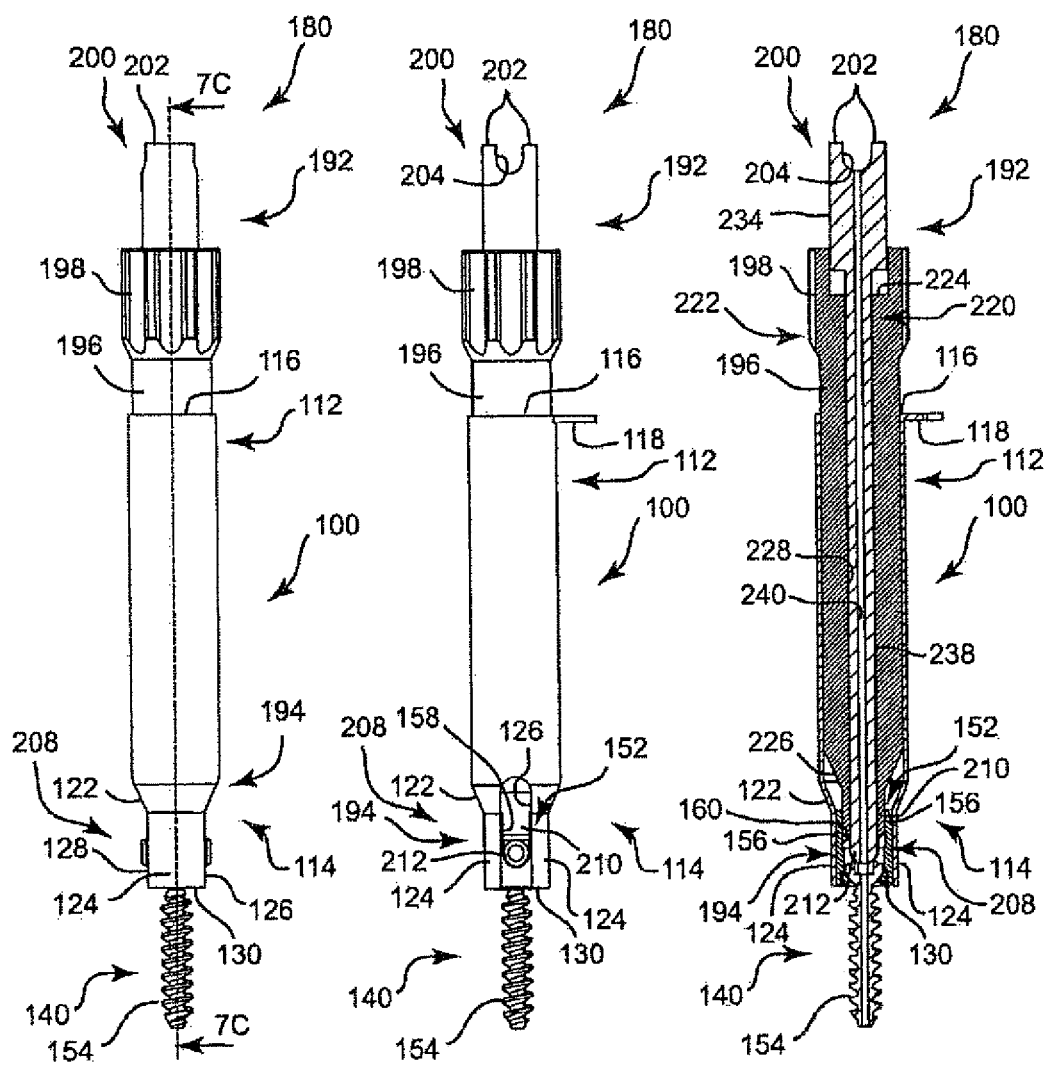
FIG. 7A is a side elevation view of the first cannula, pedicle screw, and extender of FIG. 6.
FIG. 7B is a front elevation view of the first cannula, pedicle screw, and extender of FIG. 6.
FIG. 7C is a front elevation, section view of the first cannula, pedicle screw, and extender of FIG. 6.

Referring to FIG. 6, a perspective illustrates the cannulas 100, 102, 108 and the pedicle screws 140, 142, 148 of FIG. 5, with a first extender 180, a second extender 182, and a third extender 188 inserted into engagement with the cannulas 100, 102, 108 and pedicle screws 140, 142, 148. The extenders 180, 182, 188 are used to project the anatomic points 164, 166, 168 outside the patient's body to facilitate proper contouring of the rod (not shown in FIG. 6). Thus, the space between the cannulas 100, 102, 108 need not be accessed to obtain the proper rod configuration.

In the embodiment of FIG. 6, each of the extenders 180, 182, 188 has a proximal portion 192, a distal portion 194, and a stem 196 extending between the proximal and distal portions 192, 194. The proximal portion 192 of each of the extenders 180, 182, 188 has a handle 198 that may be grasped by hand or by a tool. Additionally, each proximal portion 192 has an implant interface, which may take the form of a rod interface 200. Each rod interface 200 is shaped to receive a portion of a rod to facilitate contouring of the rod so that the contoured rod will pass through the anatomic points 164, 166, 168 within the cages 152 of the implanted pedicle screws 140, 142, 148.

Each of the rod interfaces 200 has two arms 202 that extend generally away from the remainder of the corresponding extender 180, 182, or 188. The arms 202 of each rod interface 200 define a trough 204 through which a rod (not shown in FIG. 5) can pass. The base of the trough 204 is rounded in a manner that corresponds to the radius of the rod to be retained within the cage 152 to facilitate secure retention of the rod. The arms 202 are similar in configuration to the arms 156 of the cage 152 of the corresponding pedicle screw 140, 142, 148, and the trough 204 is similar to a trough defined by the first and second slots 158, 160 of the cage 152. Accordingly, the rod interfaces 200 mimic the geometry of the cages 152 of the pedicle screws 140, 142, 148.

The distal portion 194 of each of the extenders 180, 182, 188 has a docking element 208 that may be used to facilitate engagement and relative orientation of the extenders 180, 182, 188 with the cages 152 of the pedicle screws 140, 142, 148. Each docking element 208 may include an axial stud 210 that extends along the axis of the extender 180, 182, or 188, and a transverse stud 212 proximate the distal end of the axial stud 210, that extends perpendicular to the axis of the extender 180, 182, or 188.

The extenders 180, 182, 188 represent only one of many potential extender configurations that may be used in connection with the present invention. Other extender configurations may be advantageous, particularly if the cannulas, dilators, connection elements, or guidance members employed are different from those of FIG. 6.

Alternatively, rather than providing an implant interface, extenders according to the invention may simply be used to provide a numeric measurement of relative positions or orientations of the corresponding anatomic points. Extenders may thus be incorporated into one or more measurement instruments (not shown). For example, extenders may register on the pedicle screws 140, 142, 148 and may be coupled to a series of sliders and/or rotary elements that provide linear and/or rotary measurements of the relative positions of the cages 152. Such measurements may be used to configure or select an implant. According to one example, such a measurement instrument may measure displacements between all three of the implanted cages 152 to provide a triangle, two sides of which define the path that should be followed by the axis of the rod.

Returning the configuration of FIG. 6, when the extenders 180, 182, 188 are inserted into the cannulas 100, 102, 108, the transverse studs 212 slide into the corresponding cages 152. The transverse stud 212 simulates a portion of the rod that will ultimately be retained in the cages 152; thus, the transverse stud 212 may fit relatively snugly within the corresponding cage 152. The ends of each transverse stud 212 may extend through the first and second slots 158, 160 of the corresponding cage 152 to restrict relative rotation between the cage 152 and the extender 180, 182, 188. If desired, the axial stud 210 may be sized to have relatively little clearance with the inward-facing surfaces of the arms 156 of the cage 152 so that the extenders 180, 182, 188 are constrained to remain coaxial with the cages 152. Further, the axial stud 210 may have exterior threads that threadably engage the threads on the inward-facing surfaces of the arms 156 of the corresponding cage 152.

Whether or not full axial constraint is achieved by engagement of the axial stud 210 and the transverse stud 212 with the cage 152, the cannulas 100, 102, 108 may receive the stems 196 of the extenders 180, 182, 188 with relatively little clearance such that each extender 180, 182, 188 is constrained to be coaxial with the corresponding cannula 100, 102, 108. Since the distal ends 114 of the cannulas 100, 102, 108 are docked with the cages 152, the cannulas 100, 102, 108 are coaxial with the cages 152, and the extenders 180, 182, 188 are coaxial with the cannulas 100, 102, 108 and the cages 152.

The coaxiality of the extenders 180, 182, 188 with the cages 152 enables the rod interfaces 200 to provide a linear transformation of each of the first, second, and third anatomic points 164, 166, 168 to points outside the body. More precisely, the first extender 180 projects the first anatomic point 164 along the length of the first extender 180 to a first projected point 214 within the rod interface 200 of the first extender. The second and third anatomic points 166, 168 are similarly projected to second and third projected points 216, 218. However, since the extenders 180, 182, 188 are not parallel to each other, the projected points 214, 216, 218 do not have the same spatial relationship (i.e., relative positioning) as the anatomic points 164, 166, 168.

Referring to FIG. 7A, a side elevation view illustrates the first cannula 100, the first pedicle screw 140, and the first extender 180 of FIG. 6. As shown, the ends of the transverse stud 212 of the first extender 180 may extend through the first and second slots 126, 128 of the distal end 114 of the first cannula 100 as well as through the first and second slots 158, 160 of the cage 152 of the first pedicle screw 140.

Referring to FIG. 7B, a front elevation view illustrates the first cannula 100, the first pedicle screw 140, and the first extender 180 of FIG. 6. FIG. 7B provides an end view of the transverse stud 212, illustrating how it engages the first and second slots 126, 128 of the distal end 114 of the first cannula 100 and the first and second slots 158, 160 of the cage 152 of the first pedicle screw 140.

Referring to FIG. 7C, a front elevation, section view illustrates the first cannula 100, the first pedicle screw 140, and the first extender 180 of FIG. 6. As shown, the first extender 180 may include two separate parts: a central member 220 and a sleeve member 222. The sleeve member 222 has a countersink 224 at the proximal portion 192, a taper 226 at the distal portion 194, and a lumen 228 extending between the proximal and distal portions 192, 194 to receive the central member 220.

The central member 220 may include an enlarged head 234 that fits within the countersink 224 of the sleeve member 222, a stem 238 that extends through the lumen 228 of the sleeve member 222, and a lumen 240 that passes through the stem 238. The lumen 228 is optional, and may be used to receive the first guide wire 70, particularly for the implantation method that will be set forth in connection with FIGS. 11, 12, and 13. For the present method, the lumen 228 may optionally be omitted because the guide wires 70, 72, 78 may be removed prior to insertion of the extenders 180, 182, 188.

Usage of two separate members to provide each of the extenders 180, 182, 188 enables the transverse studs 212 to be seated within the first and second slots 158, 160 of each cage 152 while the sleeve members 222 are rotated axially to threadably engage the axial studs 210 with the inward-facing surfaces of the arms 156 of the cages. The sleeve members 222 may be rotated until they press the corresponding transverse studs 212 into the first and second slots 158, 160 of the cages 152. The transverse studs 212 are then seated tightly within the cages 152 in a manner that very closely simulates the ultimate position of the rod.

Figure 8:
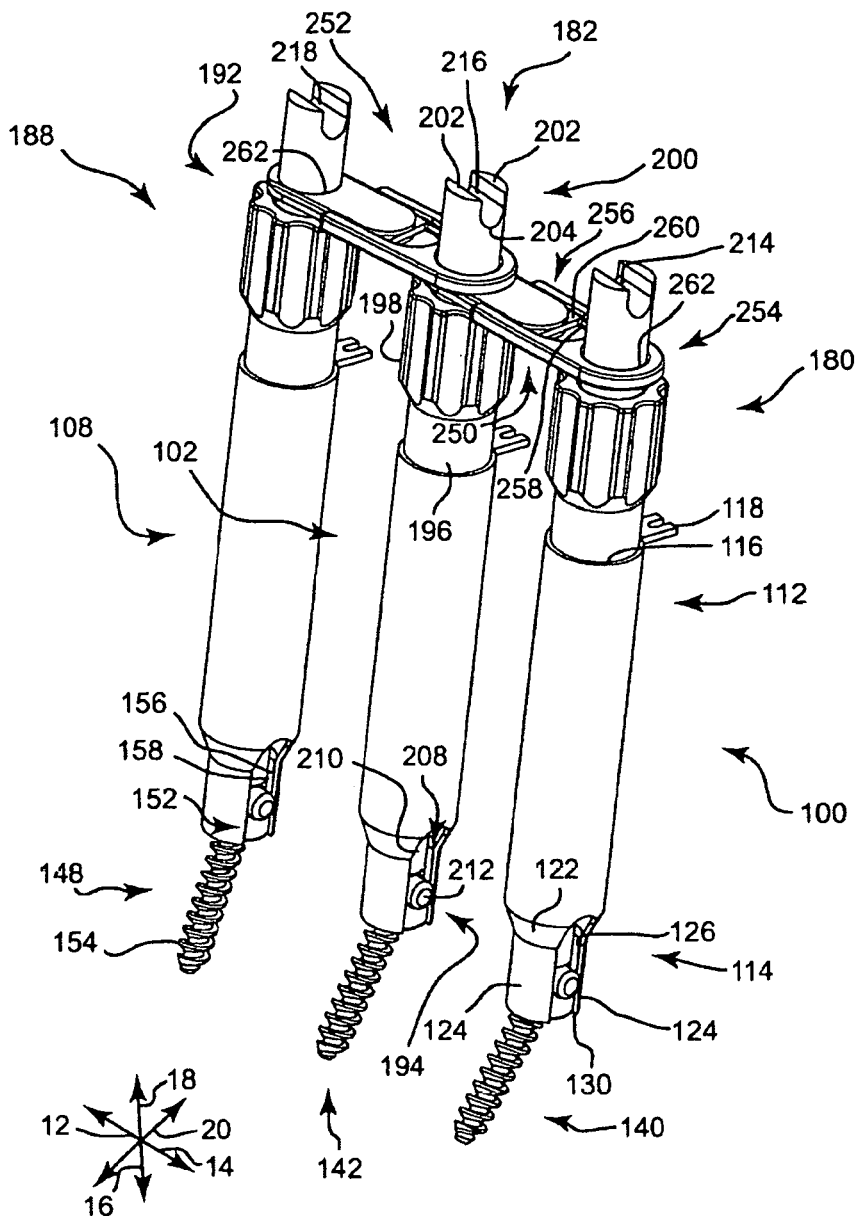
FIG. 8 is a perspective view of the cannulas, pedicle screws, and extenders of FIG. 6, with bridges used to keep the extenders in a parallel configuration.

Referring to FIG. 8, a perspective view illustrates the cannulas 100, 102, 108, pedicle screws 140, 142, 148, and extenders 180, 182, 188 of FIG. 6, with the addition of a first bridge 250 and a second bridge 252. The bridges 250, 252 are used to keep the extenders 180, 182, 188 substantially parallel to each other to constrain the spatial transformation of the anatomic points 164, 166, 168. The bridges 250, 252 are designed to constrain the extenders 180, 182, 188 only to parallelism. Thus, the bridges 250, 252 do not limit relative translation or relative axial rotation of the extenders 180, 182, 188.

Each of the first and second bridges 250, 252 has a first slider 254 and a second slider 256. The first slider 254 of each of the bridges 250, 252 has a pair of grooves 258 that face inward. The second slider 256 of each of the bridges 250, 252 has a pair of flanges 260 that extend outward into the grooves 258 of the corresponding first slider 254 so that the first and second sliders 254, 256 are linearly slidable relative to each other to permit lengthening or shortening of the bridges 250, 252. Each of the sliders 254, 256 also has an aperture 262 that fits around the enlarged head 234 of the central member 220 of the corresponding extender 180, 182, or 188. The apertures 262 are sized to fit around the enlarged heads 234 with relatively little clearance so that the bridges 250, 252 keep the extenders 180, 182, 188 parallel to each other without restricting relative axial rotation.

The bridges 250, 252 embody only one of many possible configurations that may be used in connection with the invention. According to one alternative embodiment (not shown), each bridge does not have two sliders, but has two members that are rotatably coupled to each other. Each of the members has an aperture like the apertures 262 of the bridges 250, 252, so that the bridges can permit relatively free relative translation and axial rotation of the extenders 180, 182, 188, while keeping the extenders 180, 182, 188 parallel to each other. The bridges would simply elongate and contract through the use of rotary motion instead of linear motion.

Returning to the configuration of FIG. 8, once the bridges 250, 252 have been applied, the extenders 180, 182, 188 are parallel. The projected points 214, 216, 218 then mimic the relative positioning of the anatomic points 164, 166, 168 within the body. Thus, the extenders 180, 182, 188 apply a translational spatial transformation to the anatomic points 164, 166, 168 to move them to a more accessible location without altering their positions relative to each other. Accordingly, a rod contoured such that its axis passes through the projected points 214, 216, 218 may be installed such that its axis passes through the anatomic points 164, 166, 168 to properly extend through the cages 152 of the pedicle screws 140, 142, 148.

Figure 9:
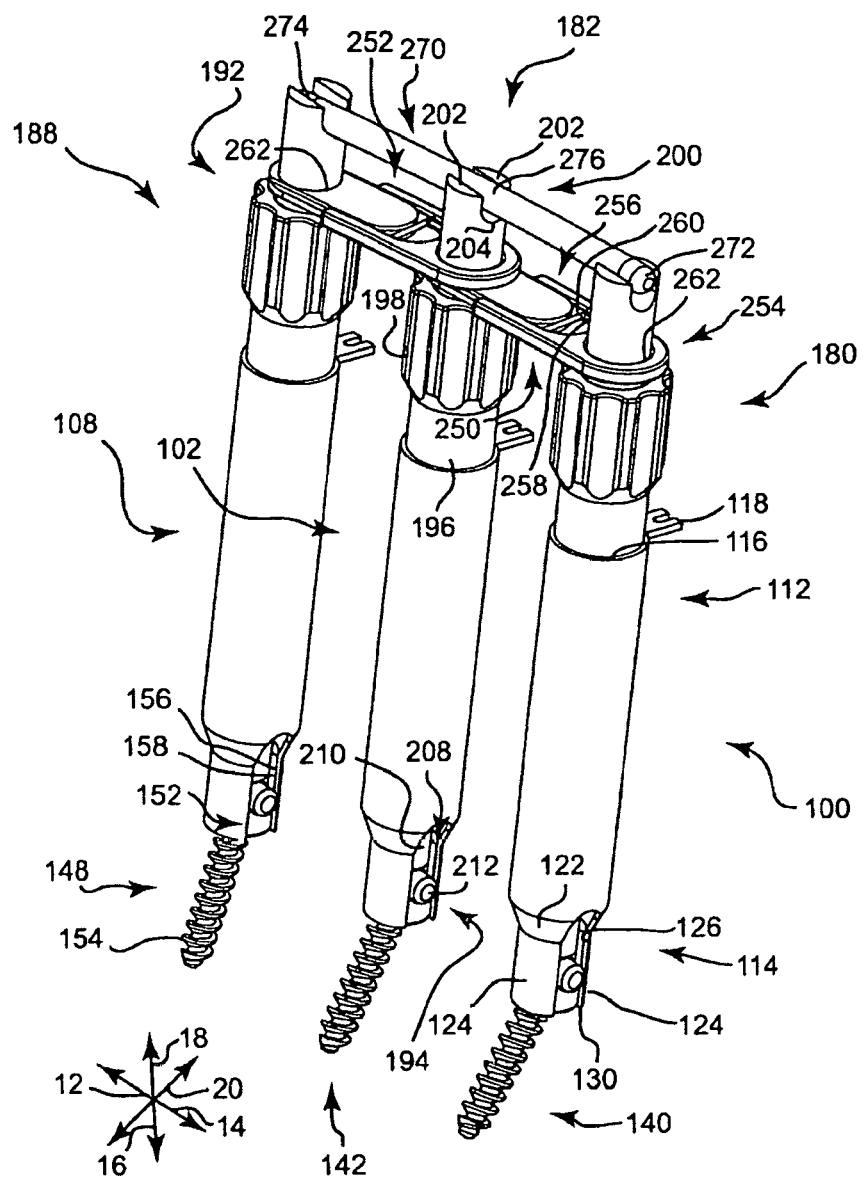
FIG. 9 is a perspective view of the cannulas, pedicle screws, extenders, and bridges of FIG. 8, with a rod seated in the rod interfaces of the extenders for contouring.

Referring to FIG. 9, a perspective view illustrates the cannulas 100, 102, 108, the pedicle screws 140, 142, 148, the extenders 180, 182, 188, and the bridges 250, 252 of FIG. 8, with a rod 270 seated in the rod interfaces 200 of the extenders 180, 182, 188 for contouring. The rod 270 has a first end 272, a second end 274, and a central portion 276. As shown, the first end 272 is positioned in the rod interface 200 of the first extender 180, the central portion 276 is positioned in the rod interface 200 of the second extender 182, and the second end 274 is positioned in the rod interface 200 of the third extender 188.

Due to natural variations in spinal morphology, the cages 152 of the pedicle screws 140, 142, 148 may not be arranged in a straight line. Thus, the rod interfaces 200 may not be arranged in a straight line. Thus, the rod 270 may need to be bent into the proper shape, for example, through the use of tooling such as pliers, a vice, or the like, so that it will lie properly within the rod interfaces 200. The process of deforming the rod 270 to the required shape may be termed "contouring."

Contouring may be carried out by, first, placing the undeformed rod 270 in the rod interfaces 200 to determine how the rod 270 should be deformed to lie properly within the rod interfaces 200. Then, the rod 270 is deformed, and again placed in the rod interfaces 200 to check the fit. This process is repeated until the rod 270 is shaped to provide an optimal fit with the rod interfaces 200.

In the alternative to contouring, the rod 270 may simply be selected from a kit or the like. For example, such a kit (not shown) may include rods bent at a variety of angles. The rod interfaces 200 could be used to select the proper rod from the kit by placing each rod, in turn, on the rod interfaces 200 until one is identified that has the proper fit. As another alternative, the rod 270 may be custom fabricated, for example, by measuring the relative positions of the rod interfaces 200 and using a CNC procedure to form the rod 270.

After the rod 270 has been configured or selected, the rod 270 and the extenders 180, 182, 188 may be removed from the operating site, leaving the pedicle screws 140, 142, 148 in place. The cannulas 100, 102, 108 may also be removed at this stage, depending on the method that will be used to implant the rod 270. The rod 270 may be inserted subcutaneously and placed on the cages 152 by making additional incisions to connect the access passageways provided by the cannulas 100, 102, 108. Alternatively, MIS (Minimally Invasive Surgical) techniques may be used to implant the rod 270 without making additional major incisions, for example, by inserting the rod 270 through the slots 126, 128 of the distal ends 114 of the cannulas 100, 102, 108.

Figure 10:
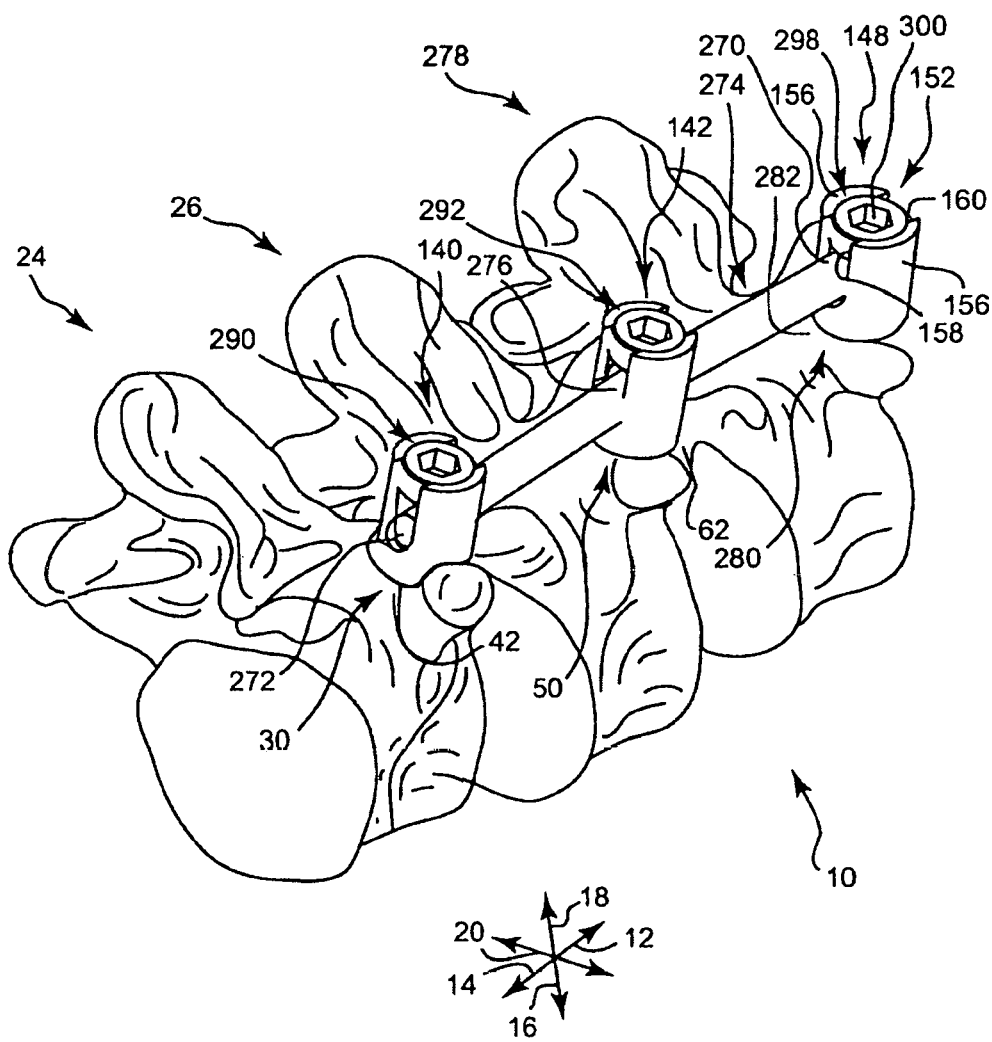
FIG. 10 is a perspective view of three adjacent vertebrae of the spine, with the rod secured to the pedicle screws to provide posterior spinal fusion.

Referring to FIG. 10, a perspective view illustrates the completed posterior spinal fusion system. In addition to the first and second vertebrae 24, 26, FIG. 10 illustrates a third vertebra 278 superior to the second vertebra 26. The third vertebra 278 has features similar to those set forth in the description of the first and second vertebrae 24, 26. Most pertinently, the third vertebra 278 has pedicles 280 with saddle points 282.

As shown, the first pedicle screw 140 is implanted in the pedicle 30 of the right side of the first vertebra 24, the second pedicle screw 142 is implanted in the pedicle 50 of the right side of the second vertebra 26, and the third pedicle screw 148 is implanted in the pedicle 280 of the right side of the third vertebra 278. The rod 270 passes through the slots 158, 160 of the cages 152 in such a manner that the axis (not shown) of the rod 270 passes through the anatomic points 164, 166, 168.

First, second, and third nuts 290, 292, 298 have been rotated into engagement with the inward-facing surfaces of the arms 156 of the cages 152 of the first, second, and third pedicle screws 140, 142, 148, respectively. The nuts 290, 292, 298 have been tightened to press the first end 272, central portion 276, and second end 274, respectively, against the heads of the screws 154 of the pedicle screws 140, 142, 148, respectively. Thus, the cages 152 are no longer freely rotatable with respect to the screws 154, but are instead locked in their current orientations.

The pedicle screws 140, 142, 148 thus cooperate with the rod 270 to restrict relative motion of the vertebrae 24, 26, 278 to form a posterior vertebral fusion system. If desired, a similar system may be implanted in the left-side pedicles 30, 50, 280 of the vertebrae 24, 26, 278 through the method set forth previously to provide a bilateral system. Additionally, the present invention is not limited to a three-level fusion system, but may be used to fuse any number of vertebrae together. To fuse more than three vertebrae together, the steps set forth above may simply be repeated for each additional vertebra, and the rod may be placed on four or more rod interfaces for configuration or selection.

The foregoing is only one of many methods encompassed within the scope of the present invention. According to one alternative method, the cannulas 100, 102, 108 may be omitted entirely from the procedure. Such a method may commence with the steps outlined above in the descriptions of FIGS. 1, 2, and 3, but may then include the steps illustrated in FIGS. 11, 12, and 13.

Referring to FIG. 11, a perspective view illustrates the guide wires 70, 72, 78 of FIG. 2, with the pedicle screws 140, 142, 148 and extenders 180, 182, 188 installed. From the step of FIG. 3, the dilators 80, 82, 88 may be removed, and the distal ends of the extenders 180, 182, 188 may be mated to the pedicle screws 140, 142, 148. More precisely, the transverse studs 212 may be inserted into the slots 158, 160, and the axial studs 210 may be threadably engaged with the inward-facing surfaces of the arms 156 in the manner set forth previously.

Then, the extenders 180, 182, 188 may be used as insertion tools to implant the pedicle screws 140, 142, 148 in the pedicles 30, 50, 280. More precisely, the extenders 180, 182, 188 are positioned to insert the proximal ends 74 of the guide wires 70, 72, 78 through the pedicle screws 140, 142, 148, and into the lumens 240 of the central members 220 of the extenders 180, 182, 188. The extenders 180, 182, 188 are advanced until the screws 154 contact the pedicles 30, 50, 280, and then the extenders 180, 182, 188 are subjected to torque and axial pressure, which may be applied to the handles 198, to implant the screws 154 in the pedicles 30, 50, 280. The guide wires 70, 72, 78 may sufficiently guide implantation of the pedicle screws 140, 142, 148 without requiring the use of the cannulas 100, 102, 108.

In the alternative to the above, the insertion tool 170 may be used in the manner described previously to implant the pedicle screws 140, 142, 148, without the use of the cannulas 100, 102, 108. The distal portions 194 of the extenders 180, 182, 188 may then be mated to the cages 152 as set forth above, after implantation of the pedicle screws 140, 142, 148.

Referring to FIG. 12, a perspective view illustrates the pedicle screws 140, 142, 148 and the extenders 180, 182, 188, with the addition of the bridges 250, 252. As described in connection with FIG. 8, the bridges 250, 252 are applied to constrain the extenders 180, 182, 188 to parallel orientations.

Referring to FIG. 13, a perspective view illustrates the pedicle screws 140, 142, 148, the extenders 180, 182, 188, and the bridges 250, 252, with the rod 270 seated in the rod interfaces 200 of the extenders 180, 182, 188 for contouring. As described in connection with FIG. 9, the rod 270 may be configured or selected by placing it in the rod interfaces 200 to ensure that it will fit properly in the cages 152 of the pedicle screws 140, 142, 148 upon implantation. After the rod 270 has been configured or selected, the additional steps set forth in the description of FIG. 9 (aside from removal of the cannulas 100, 102, 108) may be followed to obtain the fully implanted and assembled posterior spinal fusion system illustrated in FIG. 10.

The foregoing description discloses a number of different elements, any of which may be components of a system for configuring or selecting one or more implants for implantation in a body of a patient. Although the foregoing examples relate to the assembly and implantation of a posterior spinal fusion system, the present invention may be applied to a wide variety of implants, within and outside the orthopedic area. The present invention has particular benefits when an implant is to be configured or selected for a given patient, with reference to two or more anatomic points within the body.

The present invention may be embodied in other specific forms without departing from its spirit or essential characteristics. It is appreciated that various features of the systems and methods described above can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A surgical method, comprising:
    positioning a plurality of pedicle screws and associated passageway devices in a body of a patient, such that each pedicle screw is implanted in a pedicle of the spine of the patient adjacent a respective anatomic point, with each passageway device being attached to a respective pedicle screw such that each passageway device defines a longitudinal passageway through body tissue of the patient, each longitudinal passageway communicating with the respective pedicle screw and extending proximally therefrom;
    positioning an extender within each of the passageways of the plurality of passageway devices, such that a proximal portion of the extender extends out of the body and provides a spatial transformation of an associated one of the anatomic points to a location of a respective projected point defined by the proximal portion, such that the projected points indicate the relative positions of the respective implanted pedicle screws with respect to one another; and
    configuring or selecting one or more implants based on the locations of the plurality of projected points, such that the one or more implants are positionable in an implanted position engaged with each of the plurality of implanted pedicle screws.

2. The method of claim 1, wherein each of the plurality of pedicle screws includes a cage coupled to a threaded anchor portion, the cage being shaped to receive a rod, and the anchor portion being adapted to be implanted into bone, wherein the passageway devices are attached to the respective cages of the pedicle screws.

3. The method of claim 2, wherein the passageway devices are attached to the pedicle screws such that each passageway device is arranged coaxially with the cage of the respective pedicle screw.

4. The method of claim 1, further comprising docking a distal end of each passageway device to the respective pedicle screw.

5. The method of claim 1, wherein each passageway device is a cannula having a cylindrical shape.

6. The method of claim 5, wherein each passageway device defines a first slot and a second slot extending proximally along a longitudinal axis of the passageway device from a distal end of the passageway device.

7. The method of claim 6, further comprising subcutaneously inserting the one or more implants into the body of the patient through the first and second slots of at least one of the passageway devices, and securing the one or more implants to the plurality of pedicle screws.

8. The method of claim 1, wherein positioning the extender within the passageway of each of the passageway devices comprises receiving the extender within the passageway in a close concentric fit, such that the extender is constrained to be coaxial with the passageway device.

9. The method of claim 1, wherein each of the projected points is defined by a rod interface at the proximal portion of the extender.

10. The method of claim 9, wherein the rod interface defines a trough.

11. The method of claim 1, wherein positioning the extender within the passageway of each of the passageway devices comprises engaging a distal end of the extender with the respective pedicle screw.

12. The method of claim 1, further comprising deforming a rod such that the rod is positionable in a position extending through each of the plurality of projected points.

13. A surgical method, comprising:
    positioning a distal portion of a first extender proximate a first anatomic point within a body of a patient, through which one or more implants are to pass in an implanted position, the first extender having a proximal portion projecting outside the body above a skin surface of the patient when positioned;
    positioning a distal portion of a second extender proximate a second anatomic point within the body, through which the one or more implants are to pass in the implanted position, the second extender having a proximal portion projecting outside the body above the skin surface of the patient when positioned;
    deforming a rod such that the deformed rod is positionable in a projected position extending along the proximal portions of the first and second extenders; and
    positioning the deformed rod in the projected position.

14. The method of claim 13, wherein the first anatomic point is within a cage of a first pedicle screw implanted in a first pedicle of the spine of the patient, and wherein the second anatomic point is within a cage of a second pedicle screw implanted in a second pedicle of the spine.

15. The method of claim 14, further comprising mating a distal end of each of the first and second extenders with the respective first and second pedicle screws.

16. The method of claim 13, wherein positioning the deformed rod in the projected position comprises simultaneously receiving the rod in a first rod interface and a second rod interface at a respective proximal end of each of the first and second extenders.

17. The method of claim 16, wherein the first and second rod interfaces each define a respective trough.

18. The method of claim 13, further comprising constraining an orientation of the first extender with respect to the second extender to provide a spatial transformation of the first and second anatomic points to respective first and second projected points outside the body at the respective proximal portions of the first and second extenders.

19. The method of claim 18, wherein constraining the orientation of the first extender with respect to the second extender comprises coupling a first bridge to the first and second extenders to keep the first and second extenders parallel to each other while permitting substantially free relative translation between the first and second extenders.

* * * * *